US012631572B2

(12) United States Patent
Lee et al.

(10) Patent No.: US 12,631,572 B2
(45) Date of Patent: May 19, 2026

(54) BIOMATERIAL DETECTION SENSOR AND METHOD OF MANUFACTURING THE SAME

(71) Applicants:SAMSUNG ELECTRONICS CO., LTD., Suwon-si (KR); SEOUL NATIONAL UNIVERSITY R&DB FOUNDATION, Seoul (KR)

(72) Inventors: Jae Hong Lee, Suwon-si (KR); Jungwon Park, Seoul (KR); Min-Ho Kang, Seoul (KR); Minyoung Lee, Seoul (KR); Hyeong Seok Jang, Seoul (KR); Won Jong Jung, Suwon-si (KR); Jin Ha Kim, Suwon-si (KR); Kak Namkoong, Suwon-si (KR); Hyung Jun Youn, Suwon-si (KR)

(73) Assignees: SAMSUNG ELECTRONICS CO., LTD., Suwon-si (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 334 days.

(21) Appl. No.: 18/224,325

(22) Filed: Jul. 20, 2023

(65) Prior Publication Data

US 2024/0280513 A1 Aug. 22, 2024

(30) Foreign Application Priority Data

Feb. 22, 2023 (KR) .................. KR10-2023-0023925

(51) Int. Cl.
*G01N 23/06* (2018.01)
*B81B 1/00* (2006.01)
(Continued)

(52) U.S. Cl.
CPC ............. *G01N 23/06* (2013.01); *B81B 1/002* (2013.01); *B81C 1/00071* (2013.01);
(Continued)

(58) Field of Classification Search
CPC ...... G01N 23/06; G01N 33/483; B81B 1/002; B81C 1/0071
See application file for complete search history.

(56) References Cited

U.S. PATENT DOCUMENTS 8,198,071 B2 6/2012 Goshoo et al.
9,322,062 B2 4/2016 Davis et al.
(Continued)

FOREIGN PATENT DOCUMENTS

JP 2007-78631 A 3/2007
JP 2016-535589 A 11/2016
(Continued)

OTHER PUBLICATIONS

Extended European Search Report dated Apr. 17, 2024 in European Application No. 23188931.2.
(Continued)

*Primary Examiner* — Nicole M Ippolito
(74) *Attorney, Agent, or Firm* — Sughrue Mion, PLLC

(57) ABSTRACT

The present disclosure provides methods and apparatuses for biomaterial detection sensors. In some embodiments, a biomaterial detection sensor includes a membrane including a plurality of wells. Each of the plurality of wells is configured to encapsulate a biomaterial contained in a sample solution. A surface of the membrane is selectively modified into at least one of a hydrophilic surface and a hydrophobic surface. In some embodiments, a method of manufacturing a biomaterial detection sensor includes depositing a first membrane and a second membrane on respective surfaces of a wafer, forming a window by etching the first membrane and the first surface of the wafer, forming a plurality of wells on the second membrane, modifying a surface of the second membrane into at least one of a hydrophilic surface and a hydrophobic surface; and trans-
(Continued)

ferring a two-dimensional graphene oxide material onto a bottom of each of the plurality of wells.

12 Claims, 20 Drawing Sheets

(51) Int. Cl.
*B81C 1/00* (2006.01)
*G01N 33/48* (2006.01)
*G01N 33/483* (2006.01)

(52) U.S. Cl.
CPC ........ *G01N 33/483* (2013.01); *B81B 2201/05* (2013.01); *B81B 2203/033* (2013.01); *B81B 2203/0338* (2013.01); *B81C 2201/0132* (2013.01); *B81C 2201/0181* (2013.01); *B81C 2201/0198* (2013.01)

(56) References Cited

U.S. PATENT DOCUMENTS

| | | | |
|---|---|---|---|
| 9,567,630 | B2 | 2/2017 | Davis et al. |
| 10,246,743 | B2 | 4/2019 | Davis et al. |
| 10,273,536 | B2 | 4/2019 | Davis et al. |
| 11,021,745 | B2 | 6/2021 | Davis et al. |
| 11,305,282 | B2 | 4/2022 | Barany |
| 2004/0241881 | A1* | 12/2004 | Kuriger .............. G01N 27/3272 |
| | | | 427/2.11 |
| 2008/0038738 | A1* | 2/2008 | Weigum ............. A61B 5/14535 |
| | | | 435/6.12 |
| 2008/0156983 | A1* | 7/2008 | Fourrier ............ B01L 3/502792 |
| | | | 422/68.1 |
| 2009/0079976 | A1 | 3/2009 | Cunningham |

| | | | |
|---|---|---|---|
| 2010/0233429 | A1 | 9/2010 | Goshoo et al. |
| 2014/0322103 | A1 | 10/2014 | Mcdevitt et al. |
| 2015/0118707 | A1 | 4/2015 | Selvaganapathy |
| 2016/0282326 | A1 | 9/2016 | Waduge et al. |
| 2018/0299380 | A1 | 10/2018 | Makino et al. |
| 2020/0238247 | A1* | 7/2020 | Kraft ..................... C08F 220/56 |
| 2021/0229087 | A1 | 7/2021 | Zhang et al. |
| 2021/0324462 | A1 | 10/2021 | Davis et al. |
| 2022/0168742 | A1 | 6/2022 | Barany |

FOREIGN PATENT DOCUMENTS

| | | | |
|---|---|---|---|
| JP | 2022-166216 | A | 11/2022 |
| KR | 10-2015-0107231 | A | 9/2015 |
| KR | 10-2021-0142454 | A | 11/2021 |
| KR | 10-2369697 | B1 | 3/2022 |
| WO | 2015/094005 | A1 | 6/2015 |

OTHER PUBLICATIONS

Communication issued on Jan. 30, 2024 by the European Patent Office for European Patent Application No. 23188931.2.

Zhaoet al., "Droplet manipulation and microparticle sampling on perforated microfilter membranes," Journal of Micromechanics and Microengineering, vol. 18, 2008, Total 12 pages.

Kang et al., "Graphene Oxide-Supported Microwell Grids for Preparing Cryo-EM Samples with Controlled Ice Thickness," Advanced Materials (Deerfield Beach, Fla.), vol. 33, No. 43, e2102991, Sep. 2021, DOI: 10.1002/adma.202102991, Abstract only, Total 1 page.

Jackman et al., "Plasmonic Nanohole Sensor for Capturing Single Virus-Like Particles toward Virucidal Drug Evaluation," Small, vol. 12, No. 9, Mar. 2016, DOI: 10.1002/smll.201501914, Epublished Oct. 2015, Abstract only, Total 1 page.

* cited by examiner

AFTER TREATMENT WITH HMDS

HYDROPHILIC WELL (GO)

HYDROPHOBIC SURFACE

10 μm

BEFORE TREATMENT WITH HMDS

10 μm

BIOMATERIAL DETECTION SENSOR AND METHOD OF MANUFACTURING THE SAME

CROSS-REFERENCE TO RELATED APPLICATIONS

This application claims benefit of priority under 35 U.S.C. § 119 to Korean Patent Application No. 10-2023-0023925, filed on Feb. 22, 2023, in the Korean Intellectual Property Office, the disclosure of which is incorporated by reference herein in its entirety.

BACKGROUND

1. Field

The present disclosure relates generally to molecular diagnostic methods, and more particularly, to a biomaterial detection sensor and a method of manufacturing the same.

2. Description of Related Art

Recently, there has been interest in developing techniques for diagnosis and/or monitoring of biological samples. For example, clinical and/or environmental samples may be analyzed by a series of biochemical, chemical, and/or mechanical treatment processes. Related molecular diagnostic methods based on nucleic acid amplification techniques may be used in various applications, ranging, but not limited to, from diagnosis of infectious diseases and/or cancer to pharmacogenomics, development of new drugs, and the like. A polymerase chain reaction (PCR) may refer to a technique for nucleic acid amplification, which may be used as a core technology in molecular biological diagnostic methods. However, PCR may have limitations related to quantifying small amounts of viruses, since the method may have a relatively low sensitivity.

Thus, there exists a need for further improvements in molecular diagnostic methods, as the need for quantifying small amounts of viruses may be constrained by low sensitivity. Improvements are presented herein. These improvements may also be applicable to other diagnosis and/or monitoring technologies and the standards that employ these technologies.

SUMMARY

The following presents a simplified summary of one or more embodiments of the present disclosure in order to provide a basic understanding of such embodiments. This summary is not an extensive overview of all contemplated embodiments, and is intended to neither identify key or critical elements of all embodiments nor delineate the scope of any or all embodiments. Its sole purpose is to present some concepts of one or more embodiments of the present disclosure in a simplified form as a prelude to the more detailed description that is presented later.

Biomaterial detection sensors and methods of manufacturing the same are disclosed by the present disclosure.

According to an aspect of the present disclosure, a biomaterial detection sensor is provided. The biomaterial detection sensor includes a membrane including a plurality of wells. Each well of the plurality of wells is configured to encapsulate a biomaterial contained in a sample solution. A surface of the membrane is selectively modified into at least one of a hydrophilic surface and a hydrophobic surface.

In some embodiments, a diameter of each well of the plurality of wells of the biomaterial detection sensor may range from about 1 nanometer (nm) to about 10 micrometers (μm).

In some embodiments, a depth of each well of the plurality of wells of the biomaterial detection sensor may range from about 100 nm to about 500 nm.

In some embodiments, the membrane of the biomaterial detection sensor may further include a reservoir configured to receive the sample solution, and a microchannel configured to direct the sample solution from the reservoir into the plurality of wells. In such embodiments, the plurality of wells may be formed at a bottom of the microchannel.

In some embodiments of the biomaterial detection sensor, at least one of an inside of the microchannel, a wall of the microchannel, and a wall of each well of the plurality of wells may have been subjected to a hydrophilic treatment.

In some embodiments of the biomaterial detection sensor, a portion of the surface of the membrane may have been subjected to a hydrophobic treatment, and the microchannel and the plurality of wells may be disposed outside of the portion of the surface of the membrane.

In some embodiments, a width of the microchannel of the biomaterial detection sensor may be smaller than or equal to about 1 millimeter (mm). In such embodiments, the width of the microchannel may be greater than a diameter of each well of the plurality of wells.

In some embodiments, a depth of the microchannel of the biomaterial detection sensor may range from about 1 nm to about 1 mm.

In some embodiments, a material of the membrane of the biomaterial detection sensor may include at least one of silicon nitride ($Si_xN_y$), silicon dioxide ($SiO_2$), amorphous carbon, gold (Au), and silver (Ag).

In some embodiments, the biomaterial detection sensor may further include a two-dimensional (2D) material support that may include a target material of the biomaterial at a bottom of the plurality of wells.

In some embodiments, the biomaterial detection sensor may further include a layer with a window formed on one side of the membrane.

In some embodiments, the biomaterial the biomaterial detection sensor may be detectable by using at least one of a transmission electron microscope (TEM), a cryogenic TEM (cryo-TEM), an optical microscope, a confocal-optical microscope, surface-enhanced Raman spectroscopy (SERS), and surface plasmon resonance (SPR) analysis.

According to an aspect of the present disclosure, a method of manufacturing a biomaterial detection sensor is provided. The method includes depositing a first membrane on a first surface of a wafer, depositing a second membrane on a second surface of the wafer, forming a window by etching the first membrane and the first surface of the wafer, forming a plurality of wells on the second membrane, modifying a surface of the second membrane into at least one of a hydrophilic surface and a hydrophobic surface, and transferring a 2D graphene oxide material onto a bottom of each well of the plurality of wells.

In some embodiments, the forming of the window may include applying a first photoresist to a surface of the first membrane, exposing and developing the first photoresist, etching the first membrane, removing the first photoresist, and forming the window by etching a portion of the first surface of the wafer which is exposed by the etching of the first membrane.

In some embodiments, the forming of the plurality of wells may include applying a second photoresist to the surface of the second membrane, exposing and developing the second photoresist by using a well pattern mask, etching the second membrane, and removing the second photoresist.

In some embodiments, the applying of the second photoresist may include depositing silicon dioxide ($SiO_2$) on the surface of the second membrane.

In some embodiments, the forming of the plurality of wells may include forming the plurality of wells to have a predetermined diameter by using a focused ion beam (FIB) process.

In some embodiments, the modifying of the surface of the second membrane into the hydrophilic surface may include coating a wall of the plurality of wells with a hydrophilic target by using a sputtering process.

In some embodiments, the modifying of the surface of the second membrane into the hydrophobic surface may include coating a portion of the surface of the second membrane with a hydrophobic chemical solution. In such embodiments, the plurality of wells may be disposed outside of the portion of the surface of the second membrane.

In some embodiments, the method of manufacturing a biomaterial detection sensor may further include applying a third photoresist to the surface of the second membrane in which the plurality of wells are formed, exposing and developing the third photoresist by using a microchannel pattern mask, and forming a microchannel by etching an exposed portion of the second membrane to a predetermined depth.

Additional aspects are set forth in part in the description which follows and, in part, may be apparent from the description, and/or may be learned by practice of the presented embodiments.

BRIEF DESCRIPTION OF THE DRAWINGS

The above and other aspects, features, and advantages of certain embodiments of the present disclosure are to be more apparent from the following description taken in conjunction with the accompanying drawings, in which:

FIGS. 5A, 5B, 6A, 6B, and 7 illustrate examples of manufacturing a membrane structure, according to an embodiment of the present disclosure:

4

Figure 10A:
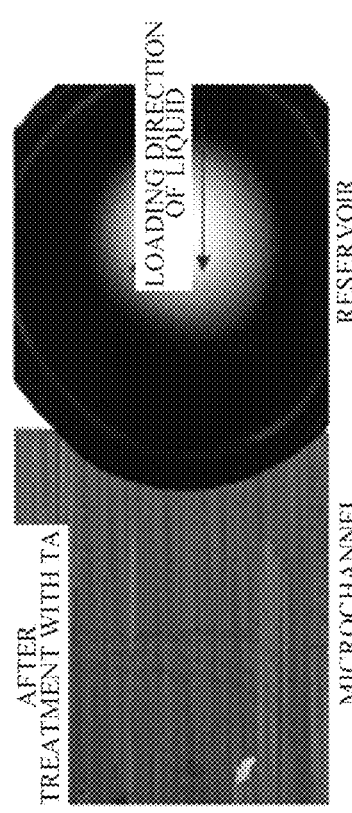
Figure 10A:
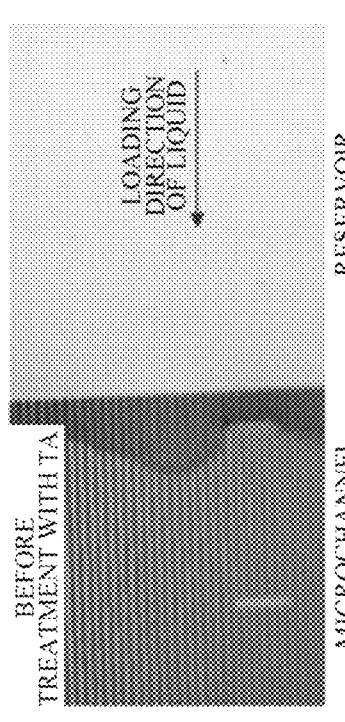
Figure 10B:
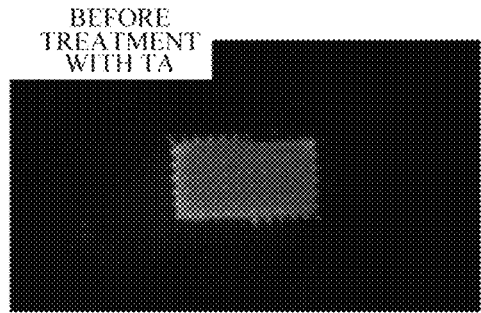
Figure 10B:
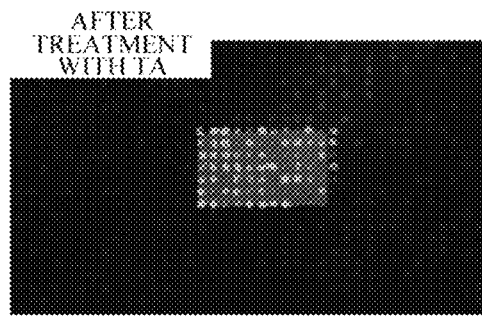
Figure 10C:
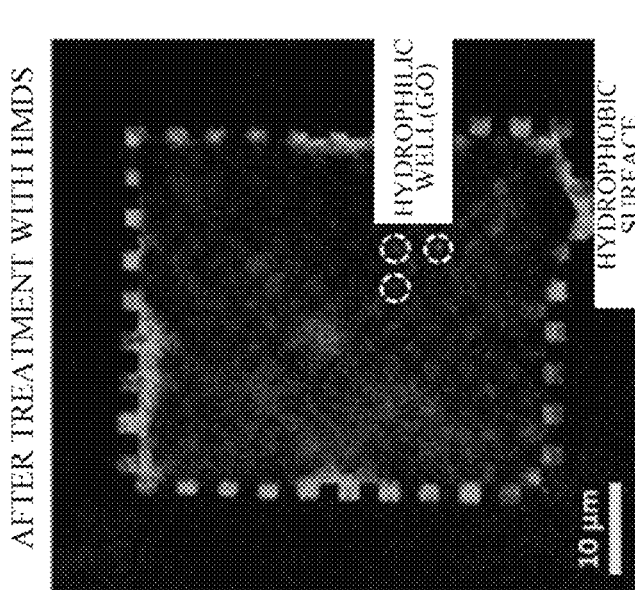
Figure 10C:
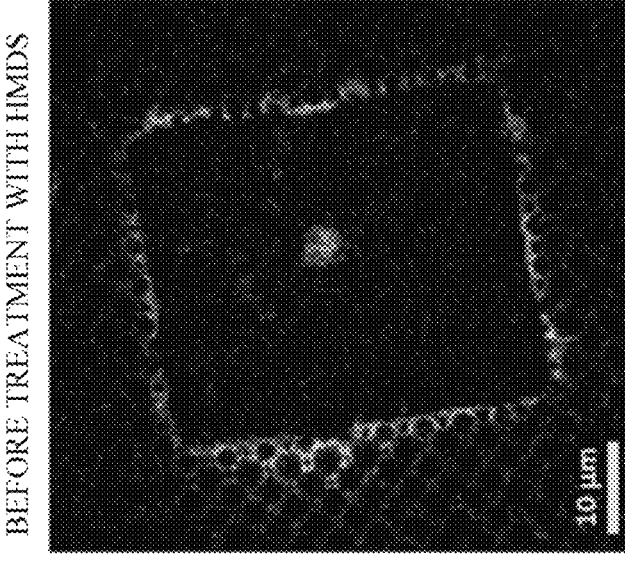
Figure 11:
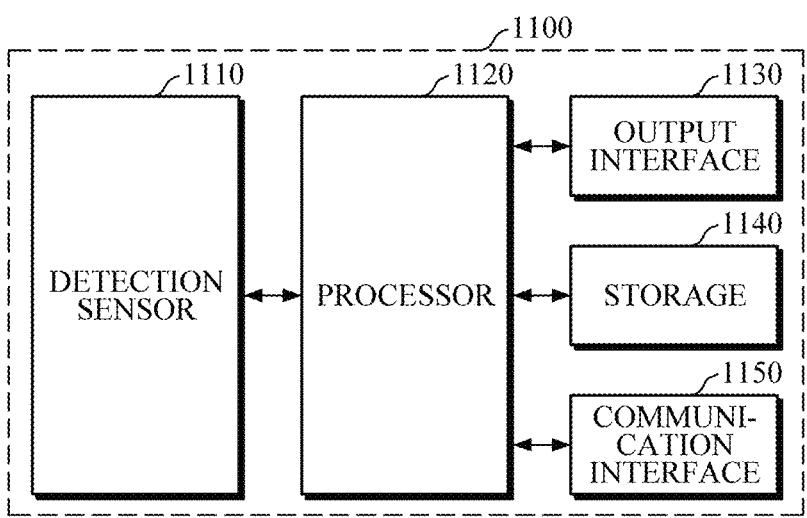

FIGS. 10A, 10B, and 10C are diagrams illustrating comparisons of membrane surfaces before and after surface modification, according to an embodiment of the present disclosure; and FIG. 11 is a block diagram illustrating an apparatus for quantifying a biomaterial concentration, according to an embodiment of the present disclosure.

DETAILED DESCRIPTION

The following description with reference to the accompanying drawings is provided to assist in a comprehensive understanding of embodiments of the present disclosure defined by the claims and their equivalents. Various specific details are included to assist in understanding, but these details are considered to be exemplary only. Therefore, those of ordinary skill in the art will recognize that various changes and modifications of the embodiments described herein may be made without departing from the scope and spirit of the disclosure. In addition, descriptions of well-known functions and structures are omitted for clarity and conciseness.

With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wired), wirelessly, or via a third element.

It will be understood that when an element or layer is referred to as being "over," "above," "on," "below," "under," "beneath," "connected to" or "coupled to" another element or layer, it may be directly over, above, on, below, under, beneath, connected or coupled to the other element or layer or intervening elements or layers may be present. In contrast, when an element is referred to as being "directly over," "directly above," "directly on," "directly below," "directly under," "directly beneath," "directly connected to" or "directly coupled to" another element or layer, there are no intervening elements or layers present.

The terms "upper," "middle", "lower", etc. may be replaced with terms, such as "first," "second," third" to be used to describe relative positions of elements. The terms "first," "second," third" may be used to described various elements but the elements are not limited by the terms and a "first element" may be referred to as a "second element". Alternatively or additionally, the terms "first", "second", "third", etc. may be used to distinguish components from each other and do not limit the present disclosure. For example, the terms "first", "second", "third", etc. may not necessarily involve an order or a numerical meaning of any form.

Reference throughout the present disclosure to "one embodiment," "an embodiment," "an example embodiment," or similar language may indicate that a particular feature, structure, or characteristic described in connection with the indicated embodiment is included in at least one embodiment of the present solution. Thus, the phrases "in one embodiment", "in an embodiment," "in an example embodiment," and similar language throughout this disclosure may, but do not necessarily, all refer to the same embodiment.

It is to be understood that the specific order or hierarchy of blocks in the processes/flowcharts disclosed are an illustration of exemplary approaches. Based upon design preferences, it is understood that the specific order or hierarchy of blocks in the processes/flowcharts may be rearranged. Further, some blocks may be combined or omitted. The accompanying claims present elements of the various blocks in a sample order, and are not meant to be limited to the specific order or hierarchy presented.

As used herein, each of the terms "$Si_3N_4$", "$SiO_2$", and the like may refer to a material made of elements included in each of the terms and is not a chemical formula representing a stoichiometric relationship.

Hereinafter, various embodiments of the present disclosure are described with reference to the accompanying drawings.

Figure 1A:
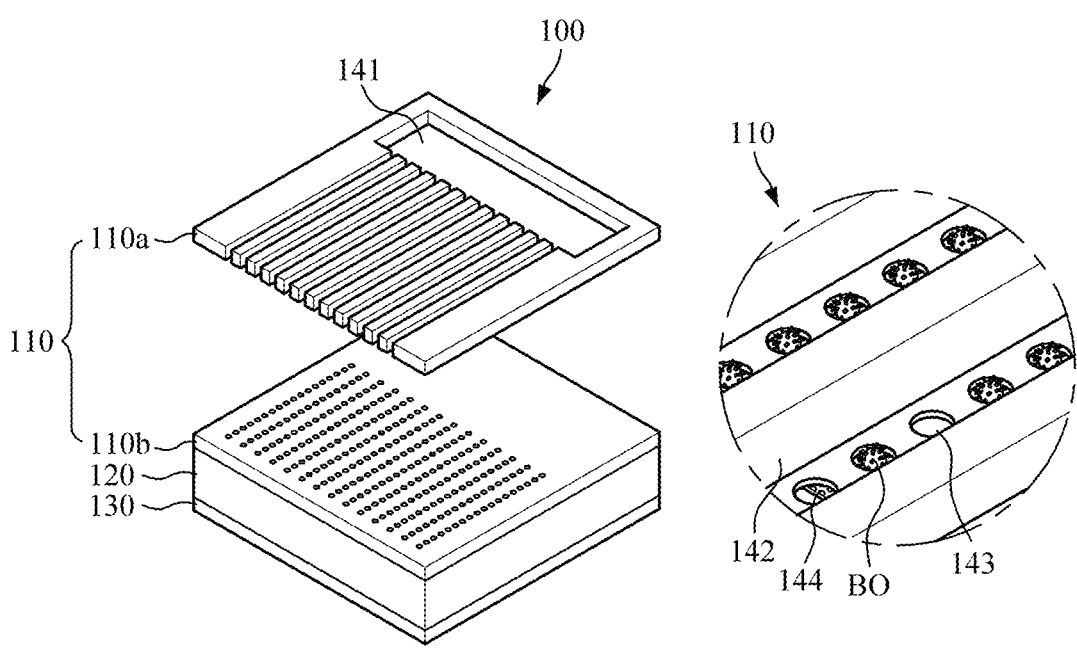
FIG. 1A is a diagram illustrating a biomaterial detection sensor, according to an embodiment of the present disclosure.
Figure 1B:
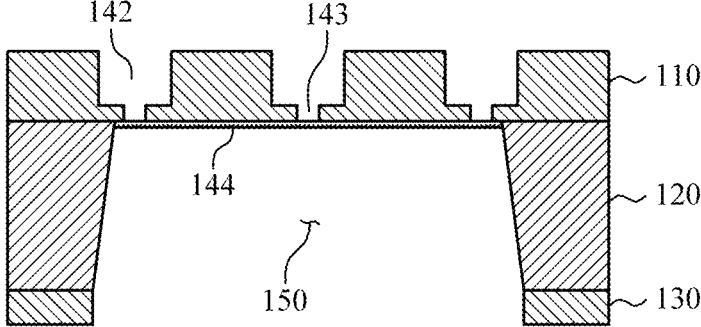
FIG. 1B is a cross-sectional diagram of the biomaterial detection sensor of FIG. 1A, according to an embodiment of the present disclosure.

FIG. 1A is a diagram illustrating a biomaterial detection sensor, according to an embodiment of the present disclosure. FIG. 1B is a cross-sectional diagram of the biomaterial detection sensor of FIG. 1A, according to an embodiment of the present disclosure.

Referring to FIGS. 1A and 1B, a biomaterial detection sensor 100 may include a membrane 110.

The membrane 110 may include a layer 110a having a reservoir 141 and/or a microchannel 142 formed therein. Alternatively or additionally, the membrane 110 may include a layer 110b having a plurality of wells 143 formed therein. As shown in FIGS. 1A and 1B, the plurality of wells 143 may be formed at the bottom of the microchannel 142. In an embodiment, the membrane 110 may be composed of materials, such as, but not limited to, silicon nitride $Si_xN_y$ (e.g., $Si_3N_4$), silicon dioxide ($SiO_2$), amorphous carbon, gold (Au), silver (Ag), a combination thereof, and the like. For example, the membrane 110 may be composed of two or more materials (e.g., $Si_xN_y$ and $SiO_2$) that may be stacked on top of each other. Alternatively or additionally, the reservoir 141 and the microchannel 142 may be formed above the plurality of wells 143, such that a sample solution may be loaded therein, and the loaded sample solution may be guided into the plurality of wells 143.

The reservoir 141, which may refer to an area where the sample solution is loaded, may have various shapes, such as, but not limited to, a circular shape, an elliptical shape, a polygonal shape (e.g., triangle, tetragon, pentagon, etc.), and the like.

The sample solution may include, but not be limited to, respiratory secretions (e.g., a biomaterial BO), bio-fluids (e.g., blood, urine, perspiration, tears, saliva, and the like), a swab sample of the upper respiratory tract, and a solution of the bio-fluid and/or the swab sample dispersed in another medium. For example, the another medium may include, but not be limited to, water, saline solution, alcohol, phosphate buffered saline solution, vital transport media, and the like.

The biomaterial may include, but not be limited to, one or a duplex of two or more of ribonucleic acid (RNA), deoxyribonucleic acid (DNA), peptide nucleic acid (PNA), locked nucleic acid (LNA), oligopeptides, proteins, toxins, and the like.

In an embodiment, the membrane 110 may include one or more microchannels 142. The microchannel 142 may have a diameter greater than a diameter of a well 143. For example, the microchannel 142 may have a width of approximately 1 millimeter (mm) or less. Alternatively or additionally, the microchannel 142 may have a depth ranging from approximately 1 nanometer (nm) to 1 mm.

In an optional or additional embodiment, when the sample solution is loaded into the reservoir 141, the sample solution may flow along each microchannel 142, and the biomaterial BO contained in the sample solution may be encapsulated within the plurality of wells 143 formed at the bottom of the microchannels 142. For example, approximately tens of thousands of wells 143 may be formed. Each of the wells 143 may have a diameter ranging from approximately 1 nm to 10 micrometers (μm). Alternatively or additionally, each of the wells 143 may have a depth ranging from approximately 100 nm to 500 nm. In an embodiment, some of the wells 143 may have different diameters and/or depths so as to encapsulate biomaterials of different sizes. For example, the wells 143 may be formed to have different sizes for each of the microchannels 143. Alternatively or additionally, the wells 143 may gradually increase in size in a flow direction of the sample solution that flows in each of the microchannels 142.

A surface of the membrane 110 may be selectively modified into at least one of a hydrophilic surface and a hydrophobic surface. For example, a wall and bottom of the microchannel 142 and/or a wall surface of the well 143 may be selectively subjected to hydrophobic treatment. In this manner, the wall and bottom of the microchannel 142 and/or the wall surface of the well 143 may have a higher hydrophilicity than other surfaces of the membrane 110, thereby increasing the probability that the sample solution remains in the well 143. Alternatively or additionally, a surface of the membrane 110, except the microchannel 142 and the well 143, may be selectively subjected to hydrophobic treatment. For example, the process of performing hydrophilic treatment on the well and/or the microchannel surface of the membrane 110 may be omitted. In this manner, fluidity of the sample solution in the microchannel 142 may be improved, thereby potentially promoting the guiding of the sample solution into the well 143 and/or preventing the biomaterial from being adsorbed on the surface of the membrane 110, except the well and/or the microchannel.

The biomaterial detection sensor 100 may further include a two-dimensional (2D) material support 144 formed at the bottom of the well 143. The 2D material support 144 may be composed of a material obtained by functionalizing graphene oxide. In an embodiment, the 2D material support 144 may contain a target material of the biomaterial. For example, the 2D material support 144 may include a 2D material film having high conductivity and/or electron transmittance in order to improve analysis with a transmission electron microscope (TEM). Alternatively or additionally, the 2D material support 144 may allow the biomaterial to be selectively combined with a target material included in the 2D material film. In an embodiment, the biomaterial may be detected based on a difference in contrast ratio of an image by analysis with the TEM.

In an embodiment, the biomaterial detection sensor 100 may further include layers (e.g., intermediate layer 120 and bottom layer 130) having a window 150 formed on one side of the membrane 110. The intermediate layer 120 may be made of silicon (Si) and/or may have a height of approximately 100 μm. The bottom layer 130 may be made of the same material as the membrane 110 and/or may have a height approximately ranging from 1,000 angstroms (Å) to 5,000 Å. However, the present disclosure is not limited in this regard. For example, the bottom layer 130 may be made of a material different from that of the membrane 110. The window 150, which may refer to an empty space, may be formed by etching some areas of the layers 120 and 130. In an embodiment, image analysis may be performed by capturing an image of the 2D material support 144 at the bottom of the well 143 through the window 150, formed as an empty space, by using the TEM.

Figure 2A:
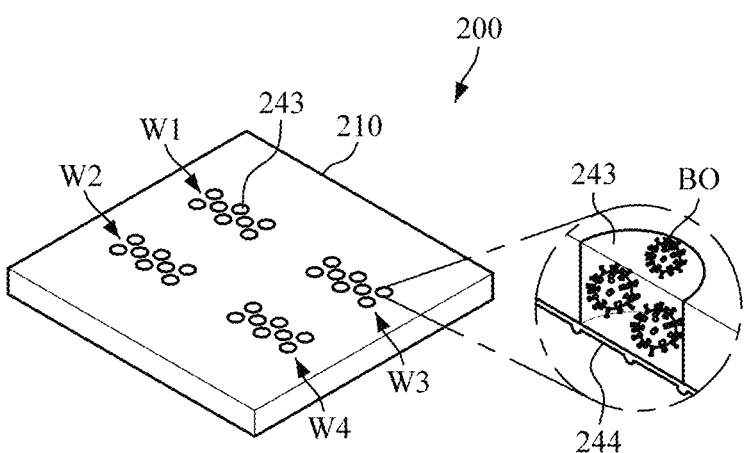
FIG. 2A is a diagram illustrating a biomaterial detection sensor, according to an embodiment of the present disclosure.
Figure 2B:
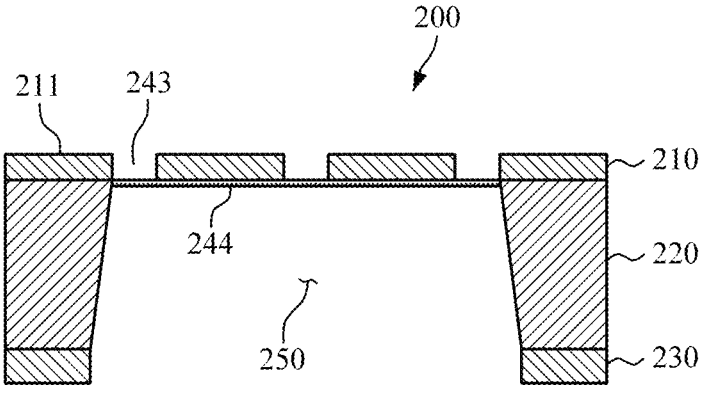
FIG. 2B is a cross-sectional diagram of the biomaterial detection sensor of FIG. 2A, according to an embodiment of the present disclosure.

FIG. 2A is a diagram illustrating a biomaterial detection sensor, according to an embodiment of the present disclosure. FIG. 2B is a cross-sectional diagram of the biomaterial detection sensor of FIG. 2A, according to an embodiment of the present disclosure. The biomaterial detection sensor 200 of FIGS. 2A and 2B may include or may be similar in many respects to the biomaterial detection sensor 100 described above with reference to FIGS. 1A and 1B, and may include additional features not mentioned above.

Referring to FIGS. 2A and 2B, the biomaterial detection sensor 200 may include a membrane 210. The membrane 210 may include a plurality of wells 243, and may omit (e.g., exclude) a microchannel. For example, the membrane 210 may include approximately tens of thousands of wells 243. Alternatively or additionally, the wells 243 may be divided into a plurality of groups (e.g., first group W1, second group W2, third group W3, and fourth group W4).

In an embodiment, a surface of the membrane 210 may be selectively subjected to hydrophilic or hydrophobic treatment. For example, a wall of each well 243 may be subjected to hydrophilic treatment, and/or a surface of the membrane 110, other than the wall of the wells 243, may be selectively subjected to hydrophobic treatment. By selectively modifying the surface of the membrane 210, the biomaterial BO may be prevented from being adsorbed on the surface of the membrane 210 other than the wells 243, and fluidity of the sample solution may be improved, thereby increasing the probability that the biomaterial is immobilized in the wells 243.

Each of the wells 243 may have a diameter approximately ranging from 1 nm to 10 μm. Each of the wells 243 may have a depth approximately ranging from 100 nm to 500 nm. Some of the wells 243 may have different diameters and/or depths so as to encapsulate biomaterials of different sizes. For example, the wells 243 may be formed to have different sizes for each of the groups W1, W2, W3, and W4. Alternatively or additionally, the wells 243 may gradually increase in size in a flow direction of the sample solution.

The biomaterial detection sensor 200 may further include a 2D material support 244 formed at the bottom of the wells 243. The 2D material support 244 may be compose of a material obtained by functionalizing graphene oxide. For example, the 2D material support 244 may contain a target material of the biomaterial.

The biomaterial detection sensor 200 may further include layers (e.g., intermediate layer 220 and bottom layer 230) having a window 250 formed on one side of the membrane 210. The intermediate layer 220 may be made of silicon (Si) and/or may have a height of approximately 100 μm. A bottom layer 230 may be made of the same material as the membrane 210 and/or may a height approximately ranging from 1,000 Å to 5,000 Å. However, the present disclosure is not limited in this regard. For example, the bottom layer 230 may be made of a material different from that of the membrane 210.

In this embodiment, the sample solution may be loaded in such a manner that after placing about 1 microliter (μl) of the sample solution on the surface of the membrane 210, the sample solution may remain for a predetermined period of time (e.g., about 60 seconds). Subsequently, after a residual (e.g., remaining) solution is absorbed with filter paper, the biomaterial detection sensor 200 may be washed several times (e.g., three (3) times) with a solvent (e.g., distilled water) and dried.

By using the aforementioned biomaterial detection sensors (e.g., biomaterial detection sensors 100 and 200) in conjunction with optical analysis of the TEM, the biomaterial may be detected with high sensitivity, and a concentration of the biomaterial may be quantified. For example, the analysis method using the TEM may have an improved spatial resolution (e.g., a few nanometers) when compared to a related optical analysis method. As a result, individual materials with a diameter of a few nanometers may be detected with improved accuracy. As described above, the number of biomaterials detected by the TEM and intensities of signals detected by optical analysis may be quantified and used in conjunction with each other, to detect the biomaterial such that sensitivity and reliability may be improved. However, the analysis is not limited thereto, and other analysis methods may be used, such as, but not limited to, a cryogenic TEM (cyro-TEM), an optical microscope, a confocal-optical microscope, surface-enhanced Raman spectroscopy (SERS), surface plasmon resonance (SPR) analysis, and the like.

Figure 3:
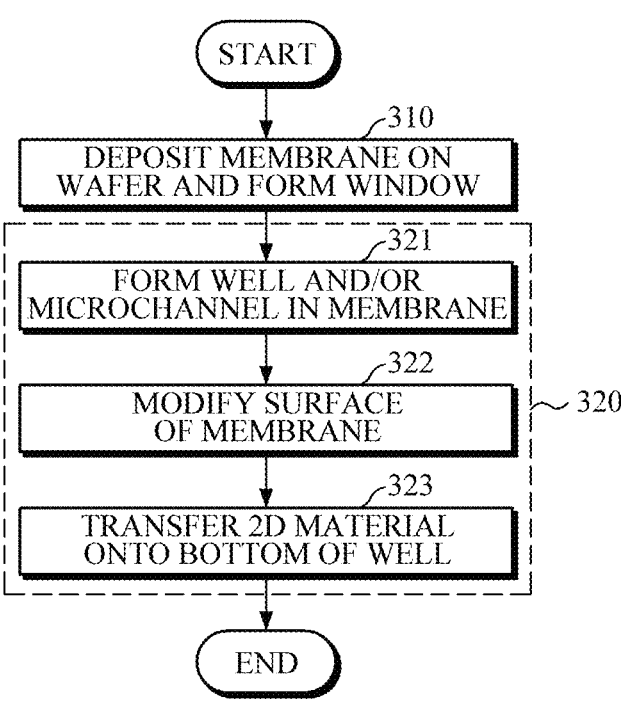
FIG. 3 is a flowchart illustrating a method of manufacturing a biomaterial detection sensor, according to an embodiment of the present disclosure.
Figure 4:
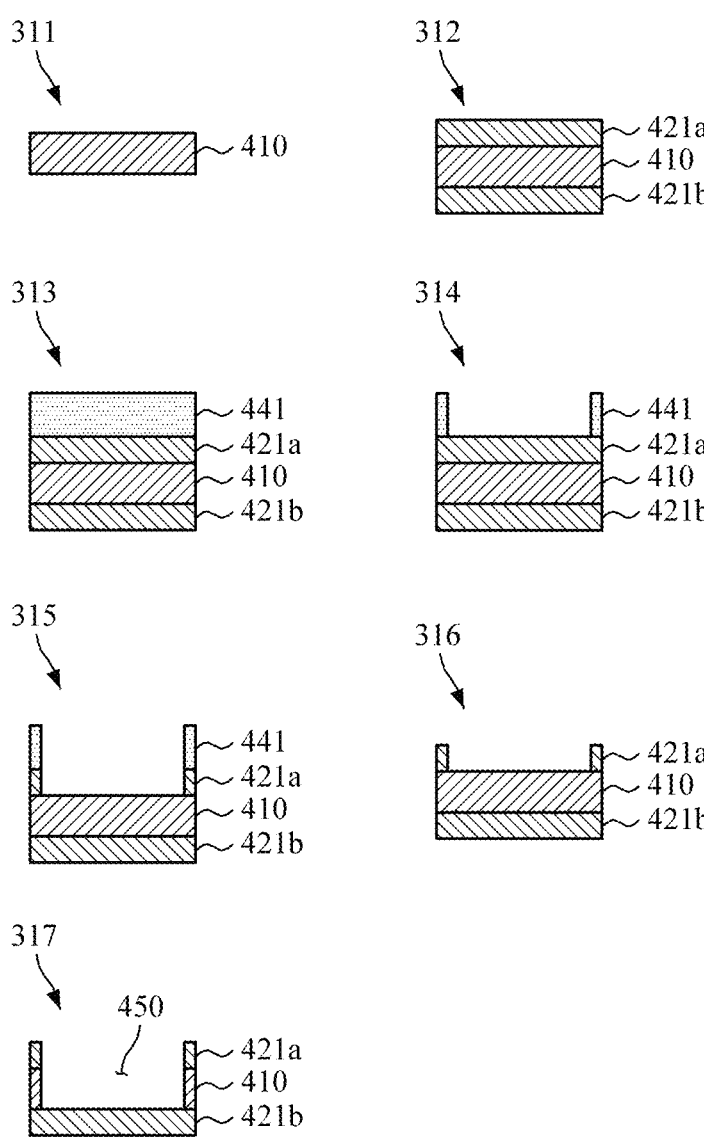
FIG. 4 is a flowchart illustrating an example of forming a window, according to an embodiment of the present disclosure.

FIG. 3 is a flowchart illustrating a method of manufacturing a biomaterial detection sensor according to an embodiment of the present disclosure. FIG. 4 is a flowchart illustrating an example of forming a window in 310 of FIG. 3. FIGS. 5A to 7 are flowcharts illustrating examples of manufacturing a membrane structure in 320 of FIG. 3.

Referring to FIG. 3, the method of manufacturing a biomaterial detection sensor may include depositing a membrane on a wafer and forming a window in operation 310 and manufacturing a membrane structure in operation 320. The manufacturing of the membrane structure in operation 320 may include forming wells and/or microchannels in the membrane in operation 321, selectively modifying a surface of the membrane in operation 322, and transferring a 2D material onto the bottom of the wells in operation 323.

An example of the forming of the window in operation 310 is described below with reference to FIG. 4.

In an embodiment, a wafer 410 may prepared in operation 311. In operation 312, a first membrane 421a and a second membrane 421b may be deposited on respective surfaces of the wafer 410. For example, the wafer 410 may include a 4-inch silicon (Si) wafer with a thickness of approximately 100 μm, which may have been prepared by using chemical mechanical polishing (CMP). After the wafer 410 is prepared, silicon nitride ($Si_xN_y$) membranes 421a and 421b may be deposited with a thickness of approximately 1000 Å to 5000 Å on respective surfaces of the wafer 410 by plasma-enhanced chemical vapor deposition (PECVD), low pressure chemical vapor deposition (LPCVD), and/or the like.

In operation 313, after applying a first photoresist 441 to a surface of the first membrane 421a on one side of the wafer 410, followed by exposure using a chrome (Cr) mask, the first photoresist 441 may be developed in operation 314.

The first membrane 421*a* may be etched by reactive ion etching (RIE) in operation 315, and the first photoresist 441 may be removed with acetone, for example, in operation 316.

In operation 317, the window 450 may be formed so that the second membrane 421*b* may be exposed. For example, the window 450 may be formed by selectively etching a portion of the wafer 410, which may have been exposed by etching the first membrane 421*a*, by using potassium hydroxide (KOH) wet etching.

Figure 5A:
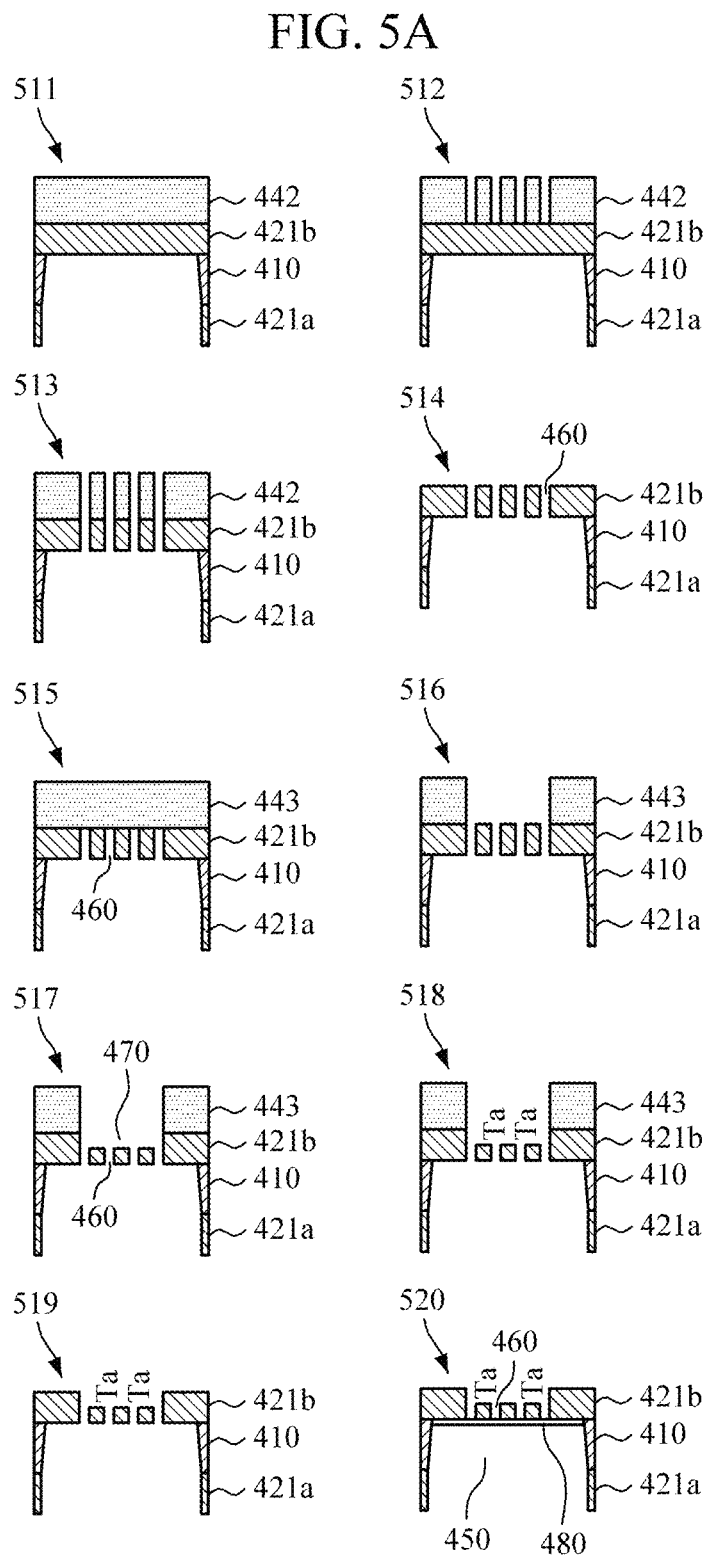

An example of the manufacturing of the membrane structure in operation 320 is described below with reference to FIG. 5A. As shown in FIGS. 4 and 5A, a biomaterial detection sensor 100 having a structure including microchannels 142 and wells 143 formed in the membrane may be manufactured.

Referring to FIG. 4, when the window 450 is formed in operation 317, a well 143 may be formed in the second membrane 421*b*. The process of forming the well 143 may include turning over the wafer 410 and applying second photoresist 442 to a surface of the second membrane 421*b* on an opposite side of the wafer 410 in operation 511, performing exposure using a well pattern mask and developing the second photoresist 442 in operation 512, etching the second membrane by (deep) reactive ion etching (DRIE/RIE) in 513, and dipping the wafer 410 in N-methylpyrrolidone (NMP) solution to remove residual second photoresist in operation 514. By changing various conditions in the exposure process, the well 460 may be adjusted to a desired diameter and position depending on design constraints based on a virus and/or biomaterial to be detected. In an embodiment, when a pattern of the well 460 is formed, the surface of the second membrane 421*b* may be turbid in color and may be seen with the naked eye. Alternatively or additionally, the formation of the well 460 and its diameter may be seen with an optical microscope.

Figure 5B:
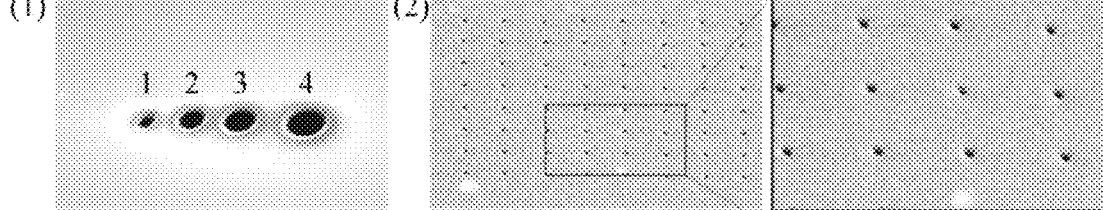

In an embodiment, the well 460 may be formed to have a desired diameter by using a focused ion beam (FIB) method in a direction of the window 450, instead of performing operations 511 to 514. As shown in FIG. 5B, (1) illustrates an example of wells formed to have various diameters 1, 2, 3, and 4 by using the FIB method, and (2) illustrates an example of wells formed to have a diameter of 130 nm by using the FIB method.

Continuing to refer to FIG. 5A, the microchannel may be formed in the second membrane 421*b*. For example, the process of forming the microchannel 142 may include applying a third photoresist 443 to the surface of the second membrane 421*b* in operation 515 having the well 460 formed therein, performing exposure by using a microchannel and reservoir pattern mask and developing the third photoresist 443 in operation 516, and forming a pattern of the microchannel 470 by etching an exposed portion of the second membrane 421*b* to a predetermined depth (e.g., 500 Å) by DRIE/RIE in operation 517.

Subsequently, the inside and wall of the microchannel 470 and/or a wall surface of the well 460 of the second membrane 421*b* may be selectively coated with tantalum (Ta) by sputtering to be subjected to hydrophilic treatment in operation 518.

In operation 519, the residual third photoresist may be removed in 519 by dipping the wafer 410 in NMP solution at a predetermined temperature (e.g., 60 degrees Celsius (° C.)). A 2D material support 480 may be formed in operation 520 by transferring a 2D graphene oxide material onto the bottom of the well 460. The 2D graphene oxide material may be obtained by functionalizing graphene oxide by mixing a target material with graphene oxide dispersed in distilled water and obtaining a supernatant liquid, except settled agglomerated particles, by carrying out centrifugation on the mixture solution of graphene oxide and the target material, followed by performing hydrophilic treatment by glow discharge on a bottom surface of a microchip, and placing approximately 3 µl of a graphene oxide solution on the surface and waiting for a predetermined time period (e.g., about 60 seconds), and then absorbing a residual solution with filter paper, followed by washing three times with distilled water and drying, for example.

Figure 6A:
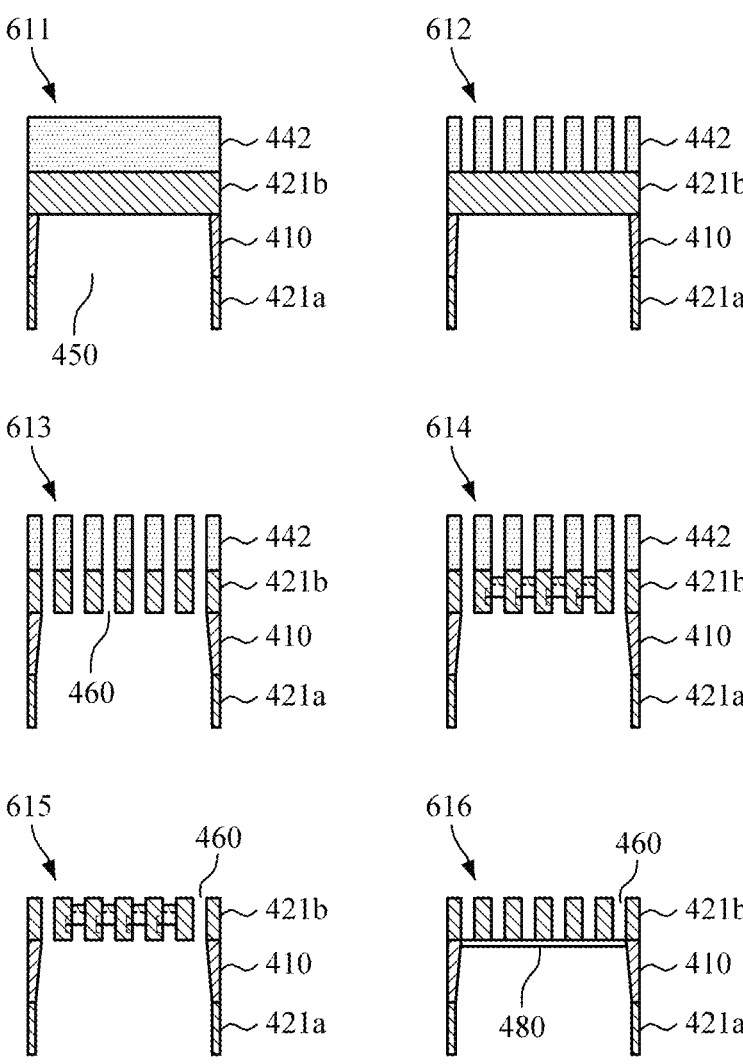
Figure 6B:
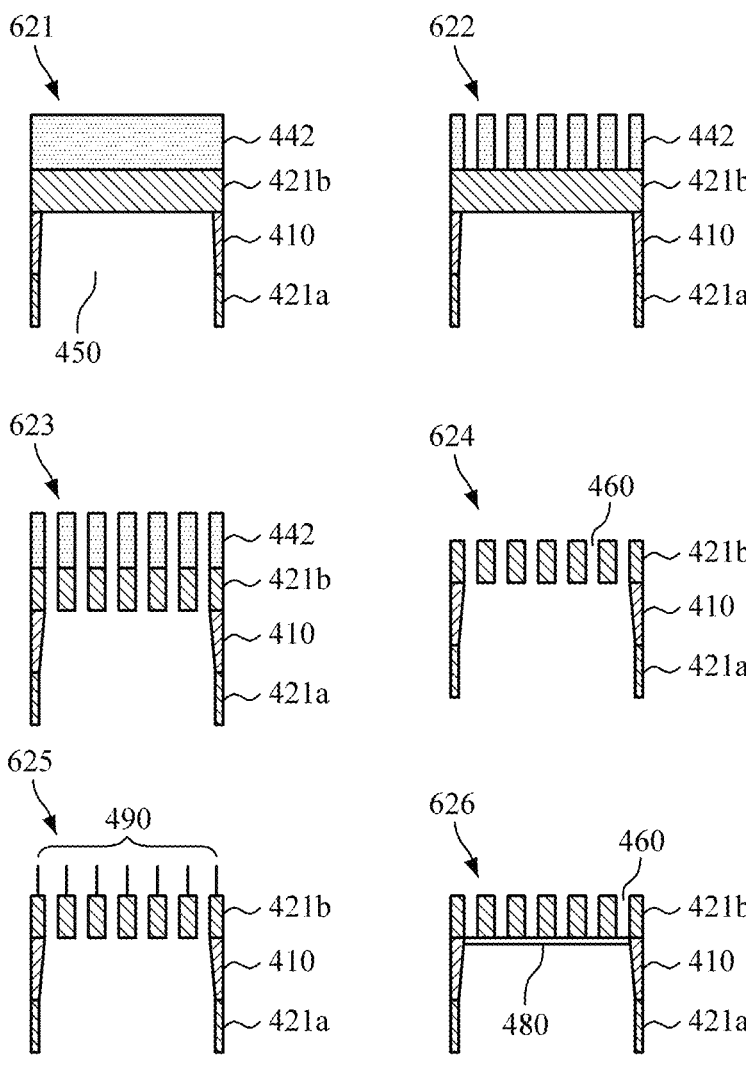

Referring to FIGS. 6A and 6B, an example of the manufacturing of the membrane structure in operation 320 is described below. In the examples of FIGS. 4 and 6A and 6B, the biomaterial detection sensor 200 of FIGS. 2A and 2B may be manufactured.

Referring to FIG. 6A, when the window 450 is formed in operation 317 in the example of FIG. 4, the wafer 410 may be turned over so that the second photoresist 442 is applied to the surface of the second membrane 421*b* on an opposite side of the wafer 410 in operation 611, exposure may be performed using a well pattern mask and the second photoresist 442 may be developed in operation 612, and the second membrane may be etched by DRIE/RIE to form the well 460 in operation 613. In an optional or additional embodiment, the well 460 may be formed to have a predetermined diameter by using the FIB method in a direction of the window 450.

In operation 614, the wall surface of the well 460 of the second membrane 421*b* may be selectively coated with tantalum (Ta) by sputtering to be subjected to hydrophilic treatment.

In operation 615, the residual second photoresist may be removed by dipping the wafer 410 in NMP solution at 60° C., for example. The 2D material support 480 may be formed in operation 616 by transferring the 2D graphene oxide material onto the bottom of the well 460.

Referring to FIG. 6B, when the window 450 is formed in operation 317 in the example of FIG. 4, the wafer 410 may be turned over so that the second photoresist 442 may be applied to the surface of the second membrane 421*b* on an opposite side of the wafer 410 in operation 621, exposure may be performed using a well pattern mask and the second photoresist 442 may be developed in 622, and the second membrane may be etched by DRIE/RIE to form the well 460 in operation 623.

In operation 624, the residual second photoresist may be removed by dipping the wafer 410 in NMP solution at 60° C., for example. The second membrane surface 490, other than the well 460, may be selectively coated with a hydrophobic material in operation 625. For example, the second membrane surface 490 may be subjected to hydrophobic treatment by spin-coating the surface with a hydrophobic chemical solution, such as hexamethyldisilizane (HMDS), parylene, polytetrafluoroethylene (PTFE), and the like, and baking the surface.

In operation 626, the 2D material support 480 may be formed by transferring the 2D graphene oxide material onto the bottom of the well 460.

Figure 7:
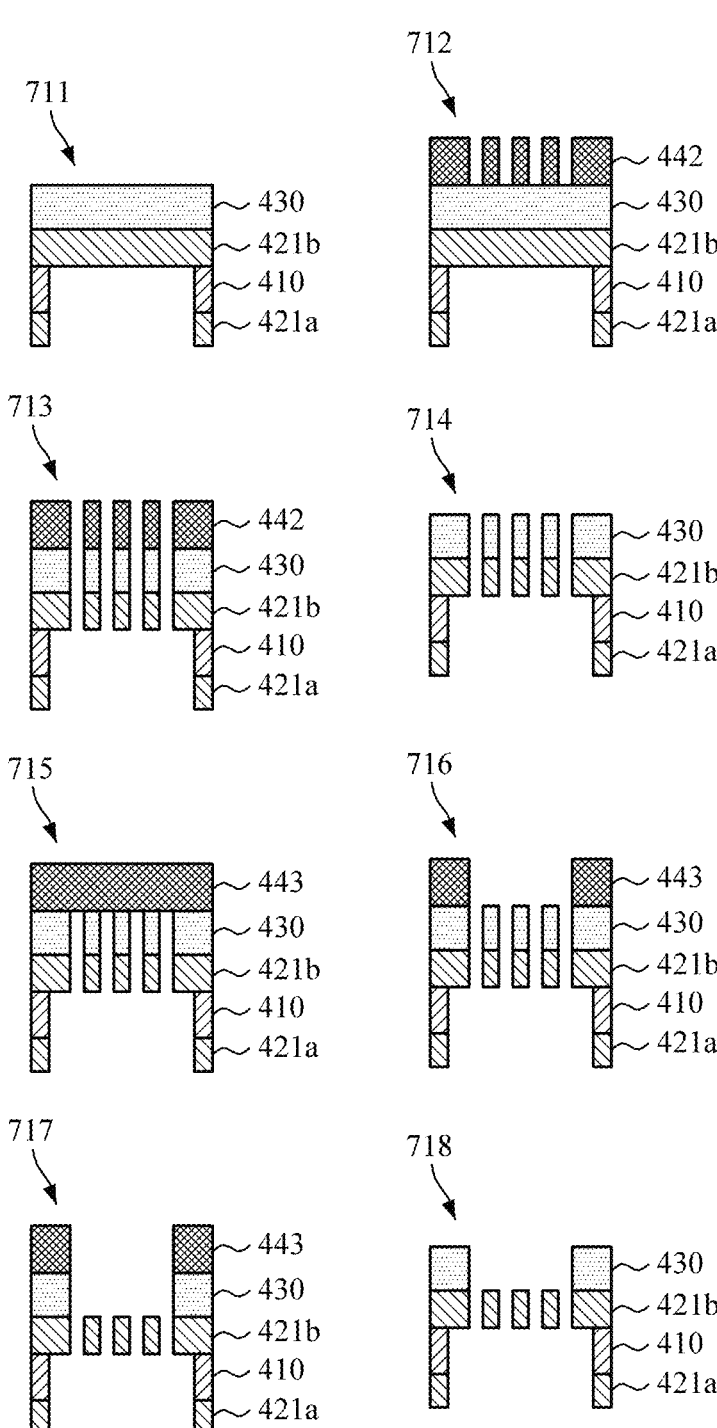

Referring to FIG. 7, an example of the manufacturing of the membrane structure in operation 320 is described below. As shown in FIGS. 4 and 7, a biomaterial detection sensor 100 having a membrane structure including microchannels 142 and wells 143 may be manufactured.

Referring to FIG. 4, when the window 450 is formed in operation 317, the wafer 410 may turned over in operation 711 so that silicon dioxide ($SiO_2$) 430 may be deposited on the second membrane 421b which may be on an opposite surface of the wafer 410. In operation 712, the second photoresist 442 may be applied to the surface of the second membrane 421b, and exposure may be performed using a well pattern mask and the second photoresist 442 may be developed. The silicon dioxide (SiO₂) 430 and the second membrane 421b may be etched by DRIE/RIE in operation 713, and the residual second photoresist 442 may be removed in operation 714 by dipping the wafer 410 in NMP solution at 60° C., for example. By forming the well 143 and the microchannel 142 by further depositing the silicon dioxide (SiO₂) 430 on the second membrane 421b, a contact angle on the surface of the well may be reduced, thereby obtaining a relatively high hydrophilicity, and a contact angle on the surface of the second membrane 421b may be increased, thereby obtaining a relatively high hydrophobicity.

In an embodiment, the operations 712 to 714 of forming the well 143 may be replaced by a process of forming the well 143 to have a predetermined diameter by using the FIB method in a direction of the window 450.

In operation 715, the third photoresist may be applied to the silicon dioxide (SiO₂) 430, exposure may be performed using a microchannel and reservoir pattern mask and the third photoresist 443 may be developed in operation 716. A microchannel pattern may be formed in operation 717 by etching an exposed portion of the silicon dioxide (SiO₂) 430 to a predetermined depth by DRIE/RIE.

In an embodiment, the inside and wall of the microchannel 470 and/or a wall surface of the well 460 of the second membrane 421b may be selectively coated with tantalum (Ta) by sputtering to be subjected to hydrophilic treatment. Then, in operation 718, the residual third photoresist may be removed by dipping the wafer 410 in NMP solution at 60° C., for example. Alternatively or additionally, the 2D material support 480 may be formed by transferring the 2D graphene oxide material onto the bottom of the well 460.

Example: Biomaterial Detection and Quantification

By using the biomaterial detection sensors (e.g., biomaterial detection sensors 100 and 200) in which a surface of a silicon nitride membrane may be selectively modified, the biomaterial may be guided into the wells and may be immobilized on the 2D material. By guiding the biomaterial to an observation area of a TEM, the biomaterial may be prevented from being adsorbed on the membrane surface. The TEM may have a spatial resolution of a few nanometers or less, and the presence of individual bioparticles with a diameter of a few nanometers may be confirmed by using the TEM. While the optical analysis may be relatively easy to use, it may also have a limited sensitivity. Accordingly, reliability of the optical analysis result may be improved by performing optical analysis in conjunction with analysis using the TEM having high spatial resolution with high detection sensitivity.

For quantifying virus particles in a sample solution, an experiment may be conducted by using a TEM and a confocal fluorescence microscope for virus solutions having different concentrations using murine leukemia virus (MLV) expressing green fluorescent protein (GFP-MLV).

The experiment process may be performed as follows.

The experiment process may include performing hydrophobic treatment on the surface of the silicon nitride membrane with HMDS, and manufacturing a biomaterial detection sensor to which graphene oxide (GO) may be transferred.

The experiment process may further include loading virus solutions into the biomaterial detection sensor (e.g., biomaterial detection sensors 100 and 200).

The experiment process may further include capturing images of the respective wells that are open to a window by using the TEM, and storing coordinates of the wells in a chip.

The experiment process may further include measuring the number of viruses in the images of the respective wells.

The experiment process may further include obtaining a spectrum by analyzing each window area in the biomaterial detection sensor by using optical analysis, and then storing coordinates of the window in a chip.

Figure 8A:
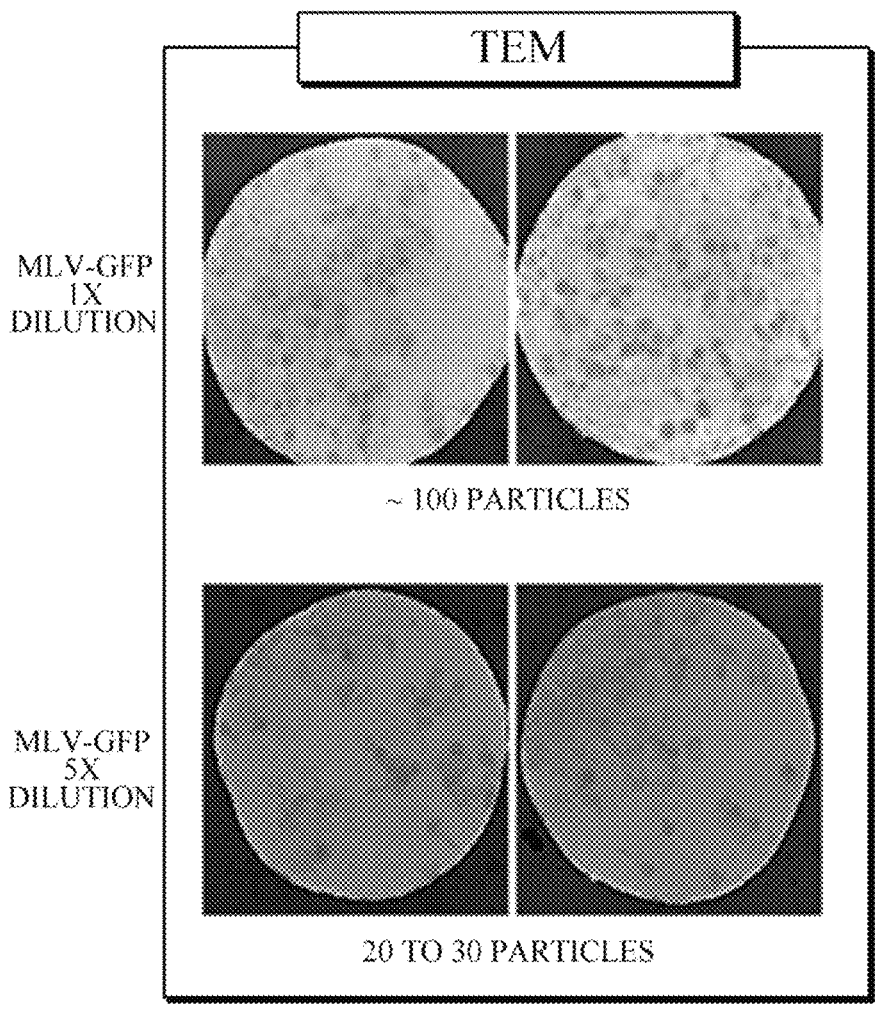
FIGS. 8A, 8B, 9A, 9B, and 9C illustrate a process of deriving a correlation between signals from a transmission electron microscope (TEM) and a fluorescence microscope, according to an embodiment of the present disclosure.
Figure 8B:
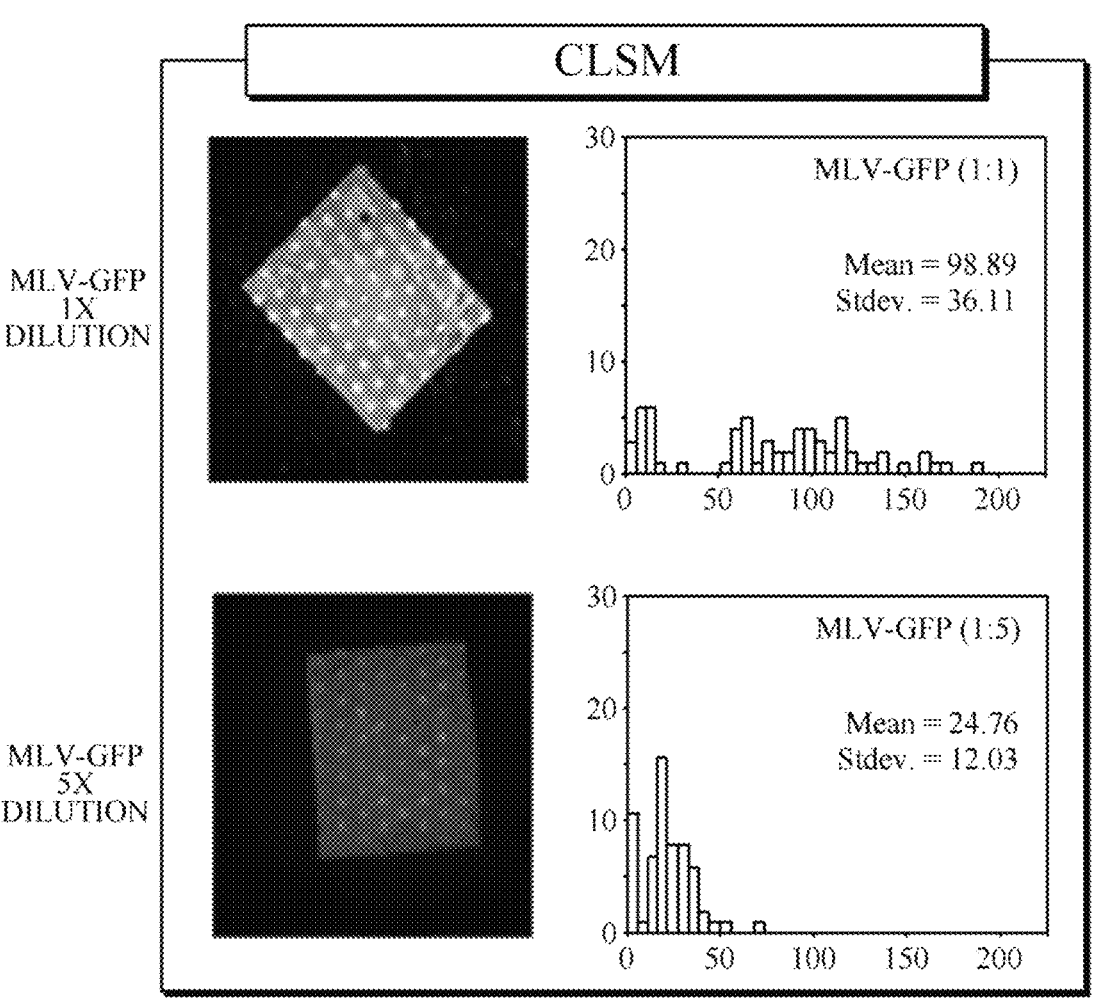

The experiment process may be used to confirm that most of the GFP-MLV were present in the wells, not on the membrane surface. For example, given two solutions having concentrations that are five times different from each other, 20 to 30 virus particles and 100 virus particles may be detected by the TEM, respectively, as shown in FIG. 8A. Alternatively or additionally, respective mean signal intensities of 24.76 and 98.89, for example, may be detected by analysis using a confocal laser scanning fluorescence microscope (CLSM), as shown in FIG. 8B.

Figure 9A:
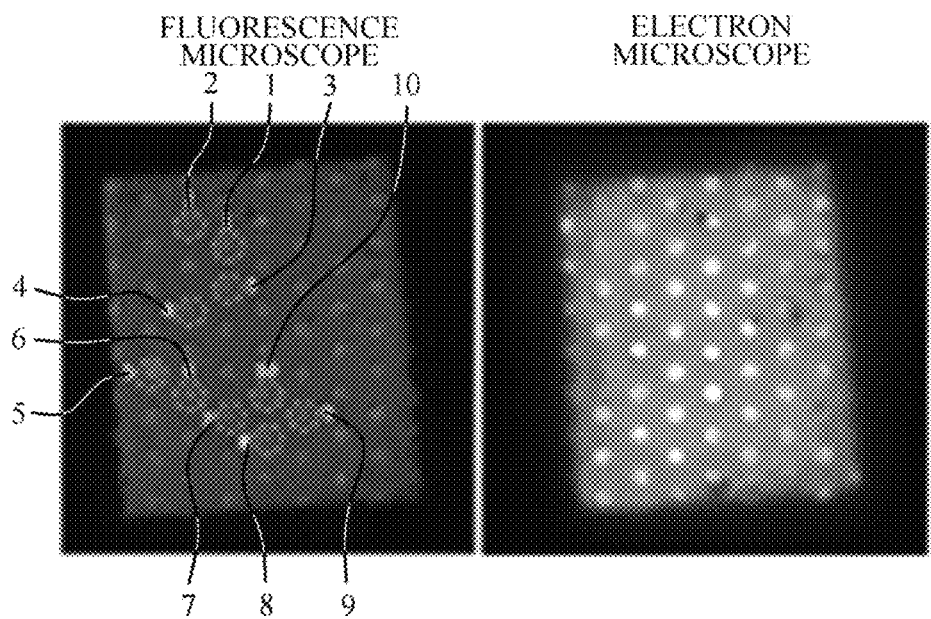
Figure 9B:
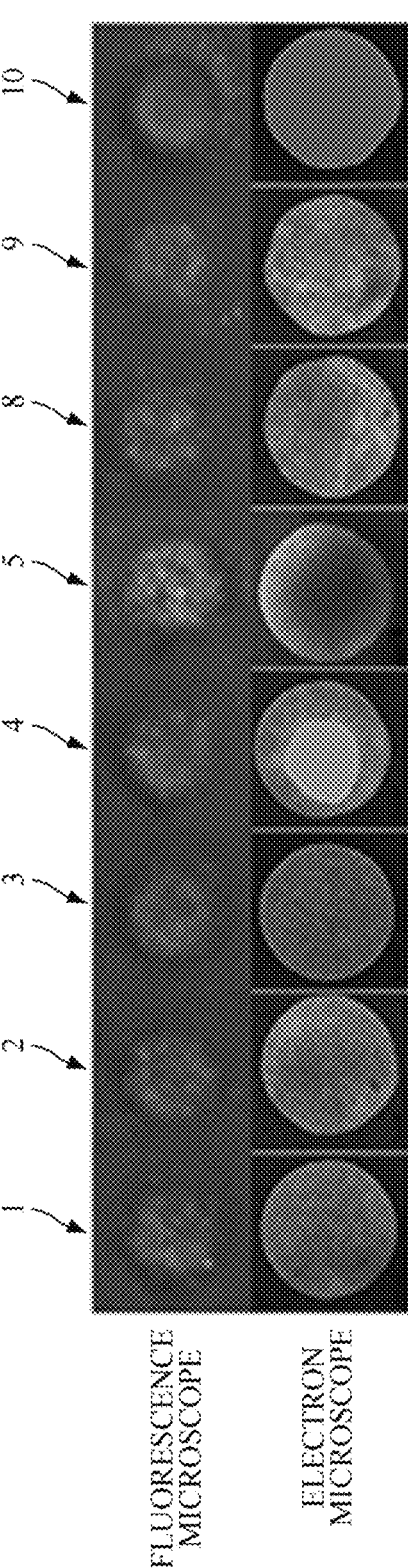
Figure 9C:
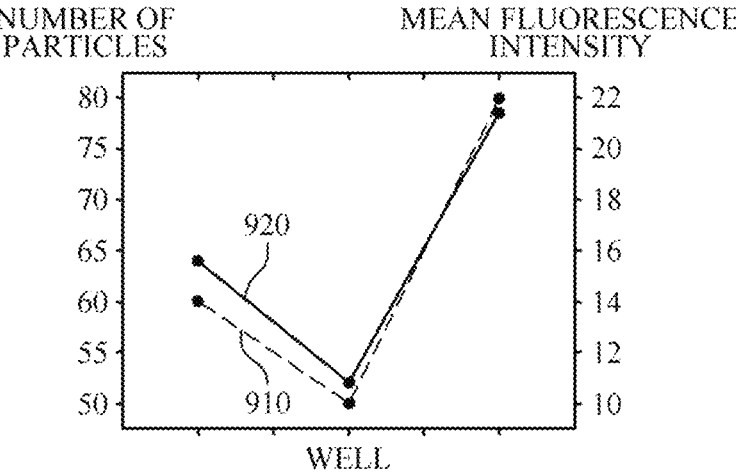

By performing signal analysis on the respective wells in the biomaterial detection sensor, a correlation between the number of viruses 910 and fluorescence signal intensities 920 in the image, acquired for the same well by the transmission electron microscope, may be derived and shown in a graph, as shown in FIGS. 9A to 9C.

The biomaterial detection sensor may include a silicon nitride membrane, having a well structure and a modified surface, and the 2D support, such that the biomaterial detection sensor may guide the biomaterial into the wells to reduce the probability that the biomaterial is adsorbed on an area that cannot be observed with the transmission electron microscope. As a result, the biomaterial may be mostly concentrated on the bottom of the 2D material support, and a relatively uniform contrast ratio of the electron microscope and optical signal may be obtained for each particle, thereby minimizing an error which may occur when the biomaterial generates different signals depending on locations on the membrane.

By using an image processing algorithm for analyzing images from the transmission electron microscope, the process of counting the number of biomaterials may be performed. In this manner, the number of biomaterials may be measured with a high spatial resolution. In addition, by correcting the signal intensity of the optical microscope based on the number of biomaterials measured by the analysis with the transmission electron microscope, the accuracy of the analysis with the optical microscope may be improved.

Comparative Example: Comparison of Membrane Surfaces Before and after Surface Modification In order to confirm the effect of Ta sputtering in a silicon nitride membrane detection sensor having a microchannel structure, fluidity of a loaded sample solution may be analyzed based on an image captured by an optical microscope. Referring to FIG. 10A, when a sample solution was loaded into a reservoir, the solution exhibited no fluidity into the channel in a detection sensor not treated with Ta, and in a detection sensor treated with Ta, the solution flows into the channel, such that the effect of improving fluidity may be confirmed.

In order to confirm the effect of improving hydrophilicity of a wall surface of wells by sputtering with Ta in a silicon nitride membrane detection sensor having a microwell structure, analysis using a confocal fluorescence microscope may be performed by loading GFP. In a detection sensor sputtered with Ta, GFP particles may have a relatively high signal intensity on the wall surface of the wells and inside the wells, and in a detection sensor not sputtered with Ta, a relatively substantial number of signals may be detected even in an area of the membrane surface, as shown in FIG. 10B.

When the surface of the silicon nitride membrane was modified into a HMDS and graphene oxide was deposited as a support on the bottom of the wells, a comparison experiment may be performed by using a confocal fluorescence microscope and GFP-MLV, in order to confirm the effect of guiding virus particles into the wells of the membrane. When the surface of the silicon nitride membrane was not modified, a fluorescence signal may be confirmed to be located on the surface of the membrane, rather than inside the wells. Accordingly, when the surface of the silicon nitride membrane was not modified, the GFP-MLV, when loaded, may be concentrated on the outside of the wells and may not be guided into the wells. By contrast, when the membrane surface was modified into a hydrophobic surface, most of the GFP-MLV were guided into the wells, as shown in FIG. 10C.

FIG. 11 is a block diagram illustrating an apparatus for quantifying a biomaterial concentration, according to an embodiment of the present disclosure.

Referring to FIG. 11, the apparatus 1100 for quantifying a biomaterial concentration may include a detection sensor 1110, a processor 1120, an output interface 1130, a storage 1140, and a communication interface 1150.

The detection sensor 1110 may include or may be similar in many respects to the biomaterial detection sensors 100 and 200 in which a surface of a membrane is selectively modified as described above. Consequently, for the sake of brevity, a detailed description of the detection sensor 1110 may be omitted.

The processor 1120 may quantify a concentration of a biomaterial encapsulated within wells of the detection sensor 1110 based on data obtained by capturing an area of a 2D material support by using a transmission electron microscope and/or an optical microscope, and the like. For example, the processor 1120 may quantify a biomaterial concentration by analyzing image data, captured by a transmission electron microscope, by using an image processing algorithm predefined by preprocessing. Alternatively or additionally, the processor 1120 may obtain a first concentration of the biomaterial by using an algorithm for analyzing a signal from an optical microscope, may obtain a second concentration of the biomaterial by analyzing image data, captured by the transmission electron microscope, by using the image processing algorithm, and may obtain a final concentration of the biomaterial by correcting the first concentration based on the second concentration by using a predefined correction equation. Alternatively or additionally, the processor 1120 may obtain a final concentration of the biomaterial by inputting the first concentration and the second concentration to a quantification model that may define a correlation between the first and second concentrations and an actual concentration of the biomaterial.

The output interface 1130 may output results of the biomaterial detection and quantification. The output interface 1130 may provide a user with information by visual, audio, and tactile methods, and the like, using a visual output module (e.g., display), an audio output module (e.g., speaker), a haptic module, and the like.

The storage 1140 may store various data necessary for the processor 1120 and/or processing results thereof. The storage 1140 may include a storage medium having at least one type of a flash memory type, a hard disk type, a multimedia card micro type, a card type (e.g., a secure digital (SD) memory, an extreme digital (XD) memory, and the like), a random access memory (RAM), a static random access memory (SRAM), a read-only memory (ROM), an electrically erasable programmable read-only memory (EEPROM), a programmable read-only memory (PROM), a magnetic memory, a magnetic disk, or an optical disk, etc., but is not limited thereto.

The communication interface 1150 may communicate with an external device to transmit and receive various data necessary for the processor 720, and/or processing results thereof. In this case, the external device may include medical equipment such as, but not limited to, a transmission electron microscope, an optical microscope, a printer to print out results, or a display device. Alternatively or additionally, the external device may include a digital television (TV), a desktop computer, a mobile phone, a smartphone, a tablet personal computer (PC), a laptop computer, a personal digital assistant (PDA), a portable multimedia player (PMP), a navigation device, an MPEG Audio Layer III (MP3) player, a digital camera, a wearable device, a smart appliance (e.g., a refrigerator, an oven), a digital virtual assistant device, and the like, but is not limited thereto.

The communication interface 1150 may communicate with the external device by using communication techniques, such as Bluetooth™ communication, Bluetooth™ low energy (BLE) communication, near field communication (NFC), WLAN communication, Zigbee communication, Infrared Data Association (IrDA) communication, ultra-wideband (UWB) communication, Ant+ communication, Institute of Electrical and Electronics Engineers (IEEE) 802.11x (Wi-Fi) communication, Wi-Fi Direct (WFD) communication, radio frequency identification (RFID) communication, cellular communications (e.g., Third Generation (3G), Fourth Generation (4G), Long Term Evolution (LTE), Fifth Generation (5G)), and the like. However, this is merely exemplary and is not intended to be limiting.

The present disclosure may be realized as a computer-readable code written on a computer-readable recording medium. The computer-readable recording medium may be any type of recording device in which data is stored in a computer-readable manner.

Examples of the computer-readable recording medium include a ROM, a RAM, a compact-disc (CD) ROM (CD-ROM), a magnetic tape, a floppy disc, an optical data storage, and a carrier wave (e.g., data transmission through the Internet). The computer-readable recording medium may be distributed over a plurality of computer systems connected to a network so that a computer-readable code may be written thereto and executed therefrom in a decentralized manner. Functional programs, codes, and code segments needed for realizing the present disclosure may be readily deduced by programmers of ordinary skill in the art to which the invention pertains.

The present disclosure has been described herein with regard to preferred embodiments. However, it is to be understood to those skilled in the art that various changes and modifications may be made without changing technical conception and essential features of the present disclosure.

Thus, it may be clear that the above-described embodiments are illustrative in all aspects and are not intended to limit the present disclosure.

What is claimed is:

1. A biomaterial detection sensor, comprising:
   a membrane comprising a plurality of wells, each well of the plurality of wells being configured to encapsulate a biomaterial contained in a sample solution,
   wherein a surface of the membrane is selectively modified into at least one of a hydrophilic surface and a hydrophobic surface, and
   wherein a size of the plurality of wells increases in a flow direction of the sample solution.

2. The biomaterial detection sensor of claim 1, wherein a diameter of each well of the plurality of wells ranges from 1 nanometer (nm) to 10 micrometers ($\mu$m).

3. The biomaterial detection sensor of claim 1, wherein a depth of each well of the plurality of wells ranges from 100 nanometers (nm) to 500 nm.

4. The biomaterial detection sensor of claim 1, wherein:
   the membrane further comprises:
      a reservoir configured to receive the sample solution; and
      a microchannel configured to direct the sample solution from the reservoir into the plurality of wells, and
   the plurality of wells are formed at a bottom of the microchannel.

5. The biomaterial detection sensor of claim 4, wherein at least one of an inside of the microchannel, a wall of the microchannel, and a wall of each well of the plurality of wells has been subjected to a hydrophilic treatment.

6. The biomaterial detection sensor of claim 4, wherein:
   a portion of the surface of the membrane has been subjected to a hydrophobic treatment, and
   the microchannel and the plurality of wells are disposed outside of the portion of the surface of the membrane.

7. The biomaterial detection sensor of claim 4, wherein:
   a width of the microchannel is smaller than or equal to about 1 millimeter (mm), and
   the width of the microchannel is greater than a diameter of each well of the plurality of wells.

8. The biomaterial detection sensor of claim 4, wherein a depth of the microchannel ranges from about 1 nanometer (nm) to about 1 millimeter (mm).

9. The biomaterial detection sensor of claim 1, wherein a material of the membrane comprises at least one of silicon nitride ($Si_xN_y$), silicon dioxide ($SiO_2$), amorphous carbon, gold (Au), and silver (Ag).

10. The biomaterial detection sensor of claim 1, further comprising:
   a two-dimensional (2D) material support comprising a target material of the biomaterial at a bottom of the plurality of wells.

11. The biomaterial detection sensor of claim 1, further comprising:
   a layer with a window formed on one side of the membrane.

12. The biomaterial detection sensor of claim 1, wherein the biomaterial is detectable by using at least one of a transmission electron microscope, a cryo-transmission electron microscope, an optical microscope, a confocal-optical microscope, surface-enhanced Raman spectroscopy (SERS), and surface plasmon resonance (SPR) analysis.

* * * * *